(12) United States Patent
Westpheling et al.

(10) Patent No.: US 6,589,732 B2
(45) Date of Patent: *Jul. 8, 2003

(54) TRANSDUCING PHAGES

(75) Inventors: Janet Westpheling, Bogart, GA (US); Julie A. Burke, Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/795,632

(22) Filed: Feb. 28, 2001

(65) Prior Publication Data

US 2002/0045239 A1 Apr. 18, 2002

Related U.S. Application Data

(63) Continuation of application No. 09/318,050, filed on May 25, 1999, now Pat. No. 6,245,504.
(60) Provisional application No. 60/126,391, filed on Mar. 26, 1999.

(51) Int. Cl.[7] .................. C12Q 1/70; C12Q 1/68; C12Q 1/02; C12N 1/12; C12N 1/20
(52) U.S. Cl. ................ 435/5; 435/6; 435/29; 435/235.1; 435/252.1; 435/472; 435/475
(58) Field of Search .............. 435/5, 6, 29, 235.1, 435/252.1, 472, 475

(56) References Cited

U.S. PATENT DOCUMENTS 6,245,504 B1 * 6/2001 Westpheling et al.
2001/0010900 A1 * 8/2001 Westpheling et al. .......... 435/5

FOREIGN PATENT DOCUMENTS

EP 0 094 506 A2 11/1983
EP 0 281 356 A1 9/1988

OTHER PUBLICATIONS

Zeph et al., Transduction of *Escherichia coli* by bacteriophage P1 in soil, 1988, Applied and Envioronmental Microbiology, pp. 1731–1737.*
Suss et al., Transduction in Streptomyces hygroscopicus mediated by the temperate bacteriophage SH10, 1981, Mol. Gen. Genet., vol. 181, pp. 552–555.*
Bedford et al., "A functional chimeric modular polyketide synthase generated via domain replacement," *Chem. Biol.*, 3:827–831 (1996).
Borman, "Combinatorial Chemistry," *C&EN*, 47–67 (Apr. 6, 1998).
Brawner et al., "Characterization of Streptomyces promoter sequences using the *Escherichia coli* galactokinase gene," *Gene*, 40:191–201 (1985).
Cane et al., "Harnessing the Biosynthetic Code: Combinations, Permutations, and Mutations," *Science*, 282:63–68 (1998).
Donadio et al., "An erythromycin analog produced by reprogramming of polyketide synthesis," *Proc. Natl. Acad. Sci. USA*, 90:7119–7123 (1993).
Goldberg et al., "Direct Selection for P1–sensitive Mutants of Eneteric Bacteria", *Journal of Bacteriology*, 118(3):810–814 (1974).
Hopwood et al., *Genetic Manipulation of Streptomyces– A Laboratory Manual*, The John Innes Foundation, Norwich, UK, pp. 8–9, 18, 21–22, 72–74, 99–102, 223, 235 (1985).
McDaniel et al., "Multiple genetic modifications of the erythromycin polyketide synthase to produce a library of novel "unnatural" natural products," *Proc. Natl. Acad. Sci. USA*, 96:1846–1851 (1999).
McHenney et al., "Gene transfer and transposition mutagenesis in *Streptomyces roseosporus*: mapping of insertions that influence daptomycin or pigment production", *Microbiology*, 142:2363–2373 (1996).
Oliynyk et al., "A hybrid modular polyketide synthase obtained by domain swapping," *Chem. Biol.*, 3:833–839 (1996).
Ripp et al., "Transduction of a freshwater microbial community by a new *Pseudomonas aeruginosa* generalized transducing phage, UT1", *Molecular Ecology*, 3:121–126 (1994).
Ruan et al., "Acyltransferase Domain Substitutions in Erythromycin Polyketide Synthase Yield Novel Erythromycin Derivatives," *J. Bact.*, 179:6416–6425 (1997).
Sambrook et al., *Molecular Cloning: A Laboratory Manual*, 2nd Ed., Cold Spring Harbor Laboratory Press, pp. 9.31–9.55, 2.65 (1989).
Sternberg et al., "Bacteriophage–mediated generalized transduction in *Escherichia coli* and *Salmonella typhimurium*", *Methods in Enzymology*, 204:18–43 (1991).

(List continued on next page.)

Primary Examiner—Remy Yucel
Assistant Examiner—Konstantina Katcheves
(74) Attorney, Agent, or Firm—Mueting, Raasch & Gebhardt, P.A.

(57) ABSTRACT

The present invention is directed to isolated transducing phages, methods of isolating transducing phages, and methods of using transducing phages including, for instance, transferring at least one nucleic acid fragment from a donor microbe to a recipient microbe, and producing a secondary metabolite from a microbe. The transducing phages typically have a broad host range, and transduce microbes in the Order Actinomycetales, in particular in the Family Streptomycetaceae, including *Streptomyces coelicolor*, *Streptomyces lividans*, *Streptomyces venezuelae*, *Streptomyces avermitilis*, and *Saccharopolyspora erythraea*. The transducing phages can be specialized transducing phages or generalized transducing phages.

42 Claims, 1 Drawing Sheet

OTHER PUBLICATIONS

Stuttard, "Localized Hydroxylamine Mutagenesis, and Cotransduction of Threonine and Lysine Genes, in *Streptomyces venezuelae*", *J. Bacteriol*, 155(3):1219–1223 (1983).

Stuttard, "Generalized Transduction in Streptomyces Species," *Genetics and Molecular Biology of Industrial Microorganisms*, Hershberger et al., (eds.), ASM, Washington, D.C. 157–162 (1989).

Süss et al., "Transduction in *Streptomyces hygroscopicus* Mediated by the Temperate Bacteriophage SH10", *Mol Gen Genet*, 181:552–555 (1981).

Vats et al., "Transductional Analysis of Chloramphenicol Biosynthesis Genes in *Streptomyces venezuelae*," *J. Bacteriol.*, 169:3809–3813 (1987).

Zeph et al., "Transduction of *Escherichia coli* by Bacteriophage P1 in Soil", *Applied and Environmental Microbiology*, 54(7):1731–1737 (1988).

* cited by examiner

TRANSDUCING PHAGES

This is a continuation of application Ser. No. 09/318,050, filed May 25, 1999, (allowed) now U.S. Pat. No. 6,245,504, which claims the benefit of U.S. provisional patent application Serial No. 60/126,391, filed Mar. 26, 1999, which are all incorporated herein by reference.

GOVERNMENT FUNDING

The present invention was made with government support under Grant No. 1021RR093161, awarded by the National Science Foundation. The Government may have certain rights in this invention.

BACKGROUND OF THE INVENTION

It would be difficult to overestimate the contribution generalized transduction has made to the study of prokaryote biology since the discovery of phage P22 in Salmonella in the early 1950s. The use of generalized transducing phages for strain construction, fine structure mapping, and genetic manipulation have played major roles in the genetic analysis of Salmonella and E. coli. One of the most important applications of generalized transduction has been to facilitate the cloning of genes identified by transposon generated mutations. The use of generalized transduction in combination with transposon mutagenesis to clone genes involved in morphogenesis has been invaluable in the study of sporulation in Bacillus subtilis.

Streptomyces are Gram-positive soil bacteria of special interest for two reasons. First, their mycelial growth mode and sporulation cycle are among the most dramatic examples of prokaryotic morphological differentiation. They grow vegetatively as multicellular, multinucleoid, branching hyphae that penetrate and solubilize orailic maiterial in the soil forming a mycelial mass. In response to environmental signals (a process that requires cell-cell communication mediated by diffusible substances), they initiate a cycle of differentiation that begins with the production of aerial hyphae that separate into uninucloid compartments that give rise to spores. Second, during the initiation of morphological development they produce a large number of secondary metabolites, including most of the natural product antibiotics used in human and animal health care. Because of its unique biology, Streptomyces offers special advantages for the study of how morphogenesis is initiated. The question of how cells within multicellular organisms sense changes in their environment and communicate that information to each other is of fundamental importance to the study of developmental biology. In spite of their interesting biology and commercial importance, relatively little is known about the gene expression pathways that regulate morphological development or antibiotic biosynthesis.

A major limitation in the study of Streptoinyces is that the typical genetic approaches for recovering genes identified by chemically induced mutations have been difficult to implement in Streptomyces. Because relatively few genetic markers exist in Streptomyces, fine structure mapping is not possible. Cloning by complementation is slow and tedious. Transformation of plasmid libraries constructed in either E. coli or Streptomyces is extremely inefficient and the libraries are often incomplete. Transposition systems have been developed in Streptomyces but they have not proved to be effective for insertional mutagenesis. This is in part due to the use of temperature sensitive plasmid vectors as transposon delivery systems. Plasmid curing is not effective and exposure to high temperatures is mutagenic in itself. This has resulted in a high background of mutations not caused by transposition. Thus, it has not been possible to determine whether a mutant phenotype was caused by transposon insertion into a gene of interest until the candidate gene was cloned, thereby permitting complementation analysis and directed disruption studies. This is not only time consuming and laborious, it is often a futile exercise because of the high background of extraneous mutations.

It has long been recognized that an efficient system for generalized transduction is needed to make transposon mutagenesis an effective genetic tool in Streptomyces. However, generalized transducing phages have not been characterized in species that can serve as genetic model systems. Attempts by many workers over the years to isolate generalized transducing phages for Streptomyces coelicolor have been uniformly unsuccessful, as have been attempts to transduce markers by the most extensively studied lytic actinomycete phages fC31, VP5, and R4. Generalized transduction has been demonstrated in Streptomyces venezuelae. This involved transduction of several markers including genes for cholemphenicol production. This was thought, however, to be an anomaly and somehow specific to Streptomyces venezuelae since the approaches used to identify transducing phages for Streptomyces venezzelae did not work for Streptomyces coelicolor.

Subsequent to the publication of much of the work describing these intraspecific generalized transducing phages of Streptomyces venezuelae and Streptomyces olivaceus, a report was authored by one of the investigators that had taken part in many of the studies. In this report titled "Generalized Transduction in Streptomyces Species," (Stuttard, In: Genetics and Molecular Biology of Industrial Microorganisms, Hershberger, et al., (eds.), pp. 157–162, ASM, Washington, D.C. (1989)) the reported "a possibly significant lack of success with Streptoinyces coelicolor and Streptoinyces lividans." The author hypothesized "that some essential host function(s), possibly expressed in few potential host strains, may be required for lytic growth of" generalized transducing particles. If such host functions are required, then generalized transducing phages will not be isolated that transduce those strains lacking the essential host functions. The author concludes that "generalized transducing phages for Streptomyces coelicolor and Streptomyces lividans remain as elusive as ever."

In the recent past there has been a significant increase in the identification of antibiotic resistant microbes. However, the identification of new antibiotics has not kept pace with the occurrence of antibiotic resistant microbes. Accordingly, there has been a significant increase in human and animal morbidity and mortality due to infectious diseases. Thus, there is a need for new antibiotics. As mentioned above, Streptomyces, and other microbes, produce secondary metabolites. Many of these secondary metabolites are natural product antibiotics used in human and animal health care. It has recently become possible to use recombinant genetic techniques to modify the metabolic pathways of microbes to result in the synthesis of new natural product antibiotics, often referred to as new natural products or non-natural products, having new activities. A limitation to this is, for instance, the need for appropriate vectors to carry large DNA fragments, and the ability to efficiently move DNA into appropriate hosts (see, for instance, Cane, D. E. et al., (1998) Science, 282, 63–68). Thus, there is a need and significant advantage to developing genetic techniques of microbes that synthesize natural product antibiotics.

SUMMARY OF THE INVENTION

The present invention is directed to a method of isolating a transducing phage, preferably, a generalized transducing phage. The method includes combining a sample containing a transducing phage with a microbe forming a first phage-microbe mixture, and incubating the first phage-microbe mixture at a temperature of less than 28° C. to form a first plaque comprising a generalized transducing phage. The invention includes a phage isolated using this method.

Another aspect of the invention is a method of isolating a transducing phage, preferably, a generalized transducing phage, involving phage DNA. The method includes combining a sample containing generalized transducing phage DNA with a microbe forming a phage DNA-microbe mixture, and incubating the phage DNA-microbe mixture at a temperature of less than 28° C. to form a first plaque comprising a transducing phage.

Another method of the invention is a method of transferring at least one nucleic acid fragment from a donor microbe to a recipient microbe. The method includes providing an isolated transducing particle comprising a nucleic acid fragment from a donor microbe, combining the transducing particle with a recipient microbe to result in a transducing particle-recipient microbe mixture, and incubating the transducing particle-recipient microbe mixture at a temperature of less than 28° C. to form a transduced recipient microbe comprising a nucleic acid fragment from the donor microbe. This method can also be used to produce a secondary metabolite, from a microbe. When a secondary metabolite is to be produced, the method further includes providing conditions effective for the recipient microbe to produce a secondary metabolite. The invention also includes a microbe prepared by this method, and a secondary metabolite produced by this method.

The invention is also directed at an isolated generalized transducing phage that can transfer at least one nucleic acid fragment from a donor microbe to a recipient microbe, wherein the frequency of transduction is at least about $10^{-7}$, and wherein the transduction of the recipient microbe occurs at less than 28° C.

A "phage" is able to inject a nucleic acid fragment into a host microbe. A type of phage is a "transducing phage." When a transducing phage infects a host microbe and replicates, two types of particles can result. One type of particle produced during the replication process is a "phage particle." As used herein, a phage particle contains a phage nucleic acid fragment and can infect another microbe and replicate, and can therefore be used as a transducing phage. The second type of particle is a "transducing particle." As used herein, a transducing particle contains at least one nucleic acid fragment derived from the host microbe. This distinction is important with respect to the discussion of superinfection killing herein. Thus, as used herein, the term phage is used generically to encompass phage that contain a phage nucleic acid fragment (i.e., a phage particle) or at least one nucleic acid fragment derived from a host microbe (i.e., a transducing particle).

Transducing particles retain the ability to inject a nucleic acid fragment into a microbe. A microbe that is the recipient of a host microbe nucleic acid fragment from a transducing particle is said to be "transduced," and is referred to herein as a "transductant."

DETAILED DESCRIPTION OF THE INVENTION

Figure 1:
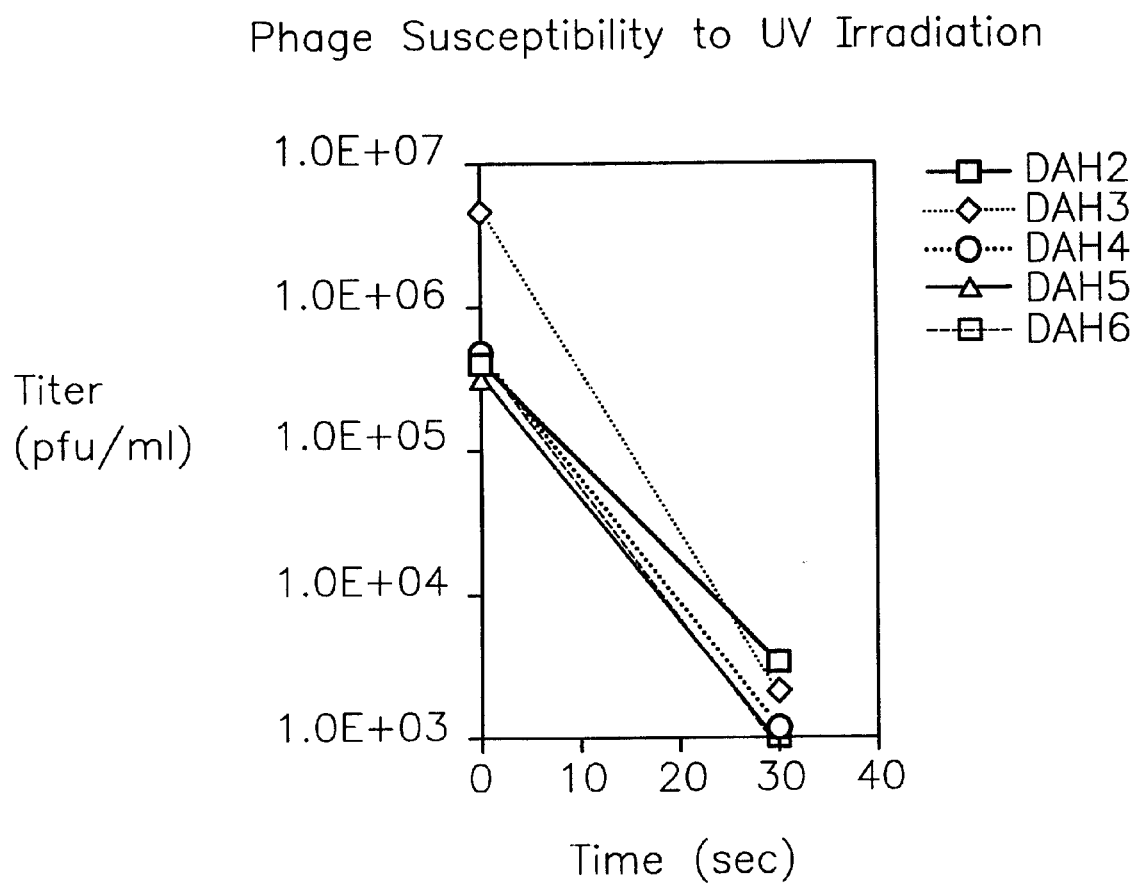
FIG. 1. Phage susceptibility to UV irradiation. The log of the phage titer is plotted versus time of exposure to UV irradiation.

The present invention is directed to isolated transducing phages and methods of isolating transducing phages. The present invention is also directed to methods of using phages including, for instance, transferring at least one nucleic acid fragment from a donor microbe to a recipient microbe, and optionally producing a secondary metabolite from a microbe. The transducing phages can be specialized transducing phages or generalized transducing phages. Preferably, they are generalized transducing phages.

A phage can include a phage nucleic acid fragment (i.e., a nucleic acid fragment containing at least a portion of a phage genome) wrapped in a protein coat. In nature, phages are not capable of growth outside microbial cells. A phage adsorbs to a microbial cell via the proteins in the coat and injects the nucleic acid fragment into the microbial cell. The phage nucleic acid fragment is replicated, transcribed, and the transcripts are used to produce protein for the production of new phage particles, i.e., more phage. Transducing phages are phages capable of generating two types of particles. One type of particle, a transducing particle, contains a nucleic acid fragment other than a phage nucleic acid fragment, e.g., a nucleic acid fragment from a host microbe. The second type of particle, a phage particle, contains only a phage nucleic acid fragment (i.e., it does not include a nucleic acid fragment from the host microbe).

When the transducing phage is a generalized transducing phage, the nucleic acid fragment present in a transducing particle can originate from different areas of the genomic DNA present in the donor, or can originate from a plasmid present in the donor. When the transducing phage is a specialized transducing phage, the nucleic acid fragment present in a transducing particle typically originates from one specific area of the genomic DNA present in the donor.

A transducing particle can be produced naturally, i.e., it is the result of the infection and subsequent lysis of a microbe infected with a transducing phage. A transducing particle can also be produced using artificial methods, including, for instance, in vitro packaging of fragmented genomic DNA. As used herein, "isolated" phage, phage particle, or transducing particle refers to a phage separated from its natural environment. Preferably, an "isolated" phage, phage particle, or transducing particle is a phage, phage particle, or transducing particle that is separated from microbes and other phage, as opposed to essentially free from agar, cellular debris, and other impurities.

The phage of the present invention, preferably a generalized transducing phage, can transfer at least one nucleic acid fragment from a donor microbe to a recipient microbe. A recipient microbe that has received at least one nucleic acid fragment from a transducing particle is referred to as transduced. A "nucleic acid fragment" as used herein refers to a polymeric form of nucleotides of any length, either ribonucleotides or deoxynucleotides, and includes both double- and single-stranded DNA (both genomic and plasmid) and both double- and single-stranded RNA. A polynucleotide fragment may include both coding and non-coding regions that can be obtained directly from a natural source (e.g., a microbe), or can be prepared with the aid of recombinant or synthetic techniques.

Significantly and preferably, the phage of the present invention transduce at a temperature of less that 28° C. More preferably, transduction occurs at, in increasing order of preference, less than about 28° C., less than about 25° C., less than about 23° C., and less than about 21° C. It is expected that the lower limit of the temperature at which transduction occurs is about 16° C. The low temperature is advantageous because it allows a significant increase in the frequency of transduction. The ability of the phage to cause transduction, preferably generalized transduction, at increased frequencies at a temperature of less that 28° C. was unexpected. Without intending to be limiting, it is believed that the decreased temperature of transduction causes decreased superinfection, particularly superinfection killing, of a transduced recipient. Other methods to decrease superinfection, particularly superinfection killing, are described herein.

Typically, the phage of the present invention transduce a recipient microbe at a frequency of transduction of at least about $10^{-7}$ (i.e., one transduced recipient per $10^7$ phage). "Frequency of transduction" refers to the number of transduced recipients (i.e., transductants) per phage particle after exposing a recipient strain to phage. Preferably, transduction occurs at, in increasing order of preference, at least about $10^{-6}$, at least about $10^{-5}$, and at least about $10^{-4}$. It is estimated that as high as about $10^{-3}$ can be achieved.

Preferably, the donor and recipient microbes are members of different families, more preferably, members of different genera, even more preferably, members of different species, and most preferably, members of the same species. This is referred to in the art as having a broad host range.

Preferably, the Families are of the Order Actinoinycedales. Preferably, the Families include Mycobacteriaceae, Actinornycetaceae, Streptomycetaceae, and Actinoplanaceae, more preferably, Streptomycetaceae. Preferably, the microbe is a spore, a mycelial fragment, a germling, a protoplast, or mixtures thereof. Many Actinomycetales naturally grow as a filament of cells. A mycelial fragment is a portion of this filament. A germling is a spore that is beginning germination as determined by the appearance of germ tubes on a spore. Preferably, members of the family Streptomycetaceae that can be transduced by the phage are Streptomyces and Saccharopolyspora. Examples of members the genus Streptomyces include *Streptomyces coelicolor, Streptomyces lividans, Streptomyces venezuelae*, and *Streptomyces avermitilis*. An example of members of the genus Saccharopolyspora includes *Saccharopolyspora erythaea*.

The phage of the present invention, preferably a generalized transducing phage, can be isolated by combining a sample containing a transducing phage with a microbe forming a first phage-microbe mixture and incubating the first phage-microbe mixture to form a first plaque comprising a transducing phage. Preferably, the incubation temperature is less than 28° C. Typically, the plaques formed by the phage of the present invention are clear or turbid. A plaque refers to an area, typically but not necessarily in a solid or semi-solid bacteriological medium, containing phage and lysed microbes. Typically, a plaque will also contain unlysed microbes that may or may not be infected with a phage nucleic acid fragment. The lysed microbes have been lysed by infection of a phage nucleic acid fragment, subsequent replication of the phage within the microbe, and then release of the replicated phage into the surrounding area by lysis of the microbe. Typically, a plaque containing predominantly lysed microbes appears to be clear (i.e., no microbes are visible), while a plaque containing unlysed microbes appears as turbid (i.e., microbes are visible). The invention is further directed to a phage prepared by this method. Preferably, phage prepared by this method is an isolated phage.

The microbe that is used to isolate a phage of the present invention can be chosen from different families as described herein. Preferably, the microbe is an Actinoinycetales.

Typically, a source of divalent cations is present during a portion of the incubation of the isolation process. Preferable divalent cations include transition metals and main group metals, and more preferably, calcium and magnesium. The sample containing a transducing phage, preferably a generalized transducing phage, can be obtained from the lithosphere and hydrosphere, including, for instance, soil, water, organic material, decomposing organic material, or volcanic ash. Preferably, a transducing phage is obtained from a composition that includes soil or volcanic ash, more preferably, soil.

Optionally, the isolation method includes separating the phage from the lithosphere or hydrosphere prior to combining the sample containing a generalized transducing phage with a microbe. For instance, separating the phage from the lithosphere can include combining a sample containing the phage, preferably a soil sample, with a diluent, preferably including water, to form a slurry and removing particles that are heavier than the phage. Particles heavier than the phage can be removed by, for instance, centrifuging the slurry. The sample can be further manipulated to remove microbes. Preferably, microbes are removed by filtration. Alternatively, microbes can be removed by adding an organic solvent, preferably chloroform, to the sample containing the phage.

The isolation method can include (and typically does include) separating the phage from the plaque to form isolated phage. For instance, the phage can be separated from the plaque by combining the first plaque with a microbe to form a second phage-microbe mixture and incubating the second phage-microbe mixture, preferably at a temperature of less than 28° C., to form a second plaque containing a transducing phage. This step can be repeated as many time as is necessary, preferably about three times, to form an isolated phage. This process is typically referred to as plaque purification.

An alternative method of isolating a transducing phage includes isolating phage DNA from a sample containing a transducing phage. This DNA can be combined with a microbe to form a phage DNA-microbe mixture and incubating the phage DNA-microbe mixture at a temperature of less than 28° C. to form a plaque comprising a transducing phage. Preferably, the microbe is an Actinomycetales, more preferably a Streptomycetaceae, most preferably a Streptomyces. Preferably, the microbe is a protoplast for this method of isolation.

The present invention is also directed to a method of transferring at least one nucleic acid fragment from a donor microbe to a recipient microbe. Preferably, the donor and recipient are Actinomycetales, more preferably a Streptomycelaceae, most preferably a Streptomyces. A method of such a transfer includes providing an isolated transducing particle comprising a nucleic acid fragment from a donor microbe. The transducing particle can be combined with a recipient microbe to result in a transducing particle-recipient microbe mixture, and the transducing particle-recipient microbe mixture incubated, preferably at a temperature of less than 28° C., to form a transduced recipient microbe, where the transduced recipient microbe contains a nucleic acid fragment from the donor microbe. The invention is further directed to a microbe prepared by this method.

The method of transferring at least one nucleic acid fragment can further include reducing superinfection, preferably superinfection killing, of the transduced recipient microbe. Superinfection of a transduced recipient refers to a recipient containing a nucleic acid fragment from a phage particle and a nucleic acid fragment from a transducing particle. The presence of phage DNA from the phage particle will typically result in lysis of the recipient. This is referred to as superinfection killing. It is advantageous to reduce superinfection, preferably superinfection killing, of a transduced recipient to increase the frequency of transduction.

Superinfection can be reduced by treating the transducing particle (which is typically in a suspension containing phage particles) prior to combining it with the recipient microbe. Preferably, the transducing particle-phage particle mixture is treated by exposing it to ultraviolet radiation. Without intending to be limiting, it is believed that the ultraviolet radiation inactivates the particles present. Since there is typically many more phage particles relative to transducing particles, more phage particles are inactivated. In general, appropriate conditions for using ultraviolet radiation include the time of exposure, the distance of the particles from the ultraviolet source, and the media the particles are in. Such conditions vary but can be easily determined by a person of skill in the art. Preferably, the wavelength is about 250 nm to about 270 nm, and more preferably about 250 nm to about 260 nm. Preferably, the intensity is about 1.9 $mW/cm^2/s$ to about 2 $mW/cm^2/s$, and more preferably it is 2 $mW/cm^2/s$.

Superinfection can also be reduced by treating the transduced recipient microbe with a chelator. Chelators useful in the present invention include citrate and ethylene glycerol-bis($\beta$-aminoethyl ether N,N,N',N',-tetraacetic acid (EGTA)). Preferably, the chelator is a source of citrate, such as sodium citrate. Chelators are preferably used at a concentration that inhibits the ability of a particle to adsorb to a microbe, but does not significantly negatively affect the viability of the microbe. This concentration typically varies depending on the chelator used, but can be easily determined by a person of skill in the art. Typical concentrations of citrate are from about 1 mM to about 50 mM, preferably about 10 mM. Superinfection can also be reduced by combining low temperature and a chelating agent, or low temperature and ultraviolet radiation, or all three.

An isolated transducing particle that includes a nucleic acid fragment from a donor microbe can be obtained by several methods. For instance, an isolated phage, preferably a transducing phage, can be combined with a donor microbe to form a phage-donor microbe mixture. This phage-donor microbe mixture can be incubated, preferably at less than 28° C., to form transducing particles. Alternatively, a transducing particle can be produced using artificial methods, for instance, in vitro packaging. Preferably, the isolated transducing particle is provided in a suspension of phage comprising isolated transducing particles. In general, the higher the concentration of transducing particles that are combined with a recipient microbe, the higher the probability of forming a transduced recipient microbe that contains a nucleic acid fragment from the donor microbe. Preferably, the concentration of the transducing particles in the suspension of phage is, in increasing order of preference, at least about 1 in $10^8$ (1 transducing particle in $10^8$ phage particles), at least about 1 in $10^7$, at least about 1 in $10^6$, at least about 1 in $10^5$, at least about 1 in $10^4$, and at least about 1 in $10^3$.

A nucleic acid fragment from a donor microbe can contain a non-coding region, a coding region or a portion thereof, or a mixture thereof. Preferably, the nucleic acid fragment from a donor microbe includes at least one coding region. A "coding region" is a linear form of nucleotides that typically encodes a polypeptide, usually via mRNA, when placed under the control of appropriate regulatory sequences (e.g., a promoter). The boundaries of a coding region are generally determined by a translation start codon at its 5' end and a translation stop codon at its 3' end, or a transcriptional start site at the 5' end and a translational stop codon or a transcriptional stop site at the 3' end.

A coding region may encode a polypeptide or a transcript (i.e., an RNA transcript) that is involved in the synthesis of a metabolite, or polypeptides that impart antibiotic resistance or catalyze the synthesis of an antibiotic (e.g., lincomycin, or rifampicin). A metabolite includes primary metabolites (i.e., the products or intermediates of a primary metabolic pathway), and secondary metabolites (i.e., products or intermediates of a secondary metabolic pathway). As used herein, "metabolic pathway" includes primary metabolic pathways and secondary metabolic pathways. A "polypeptide" as used herein refers to a polymer of amino acids and does not refer to a specific length of a polymer of amino acids. Thus, for example, the terms peptide, oligopeptide, protein, structural protein (e.g., one of several polypeptides in a multimeric complex) and enzyme are included within the definition of polypeptide. A polypeptide can be involved in, e.g., the catalysis of a product or intermediate, or the transport or anchoring of a product or intermediate. A polypeptide can also be involved in, e.g., holding a multimeric complex together, or post-synthesis steps of a product, e.g., transport of a product.

Using the methods of the present invention, a recipient microbe can be transduced so that it expresses polypeptides not produced by the recipient microbe prior to transduction. Alternatively, a recipient can be transduced so that it expresses a polypeptide in different amounts (increased or decreased) than the microbe could prior to transduction. This method is expected to allow the construction of microbes that have altered metabolic pathways. This is sometimes referred to in the art as "metabolic engineering." For instance, the transduced recipient microbe can produce a metabolite, a secondary metabolite, or a polypeptide at a different level, either higher or lower, than is produced by the recipient microbe prior to transduction. A nonlimiting example of this is the transduction of a recipient to produce increased levels of acetyl-CoA. In this transduced recipient producing increased levels of acetyl-CoA it is further expected that the amounts of products of metabolic pathways that use acetyl-CoA will be increased.

The present invention can be used to transfer at least one nucleic acid fragment containing a coding region that encodes a marker, including, for example, one that can complement a mutation present in a recipient or encodes an antibiotic. When a marker that complements a mutation is transferred to a recipient, preferably the transduction of the marker occurs at a frequency that is greater than the normal mutation rate (i.e., reversion frequency) for a marker. For example, as shown in the Examples, the reversion frequency of the arg mutation in a recipient strain is <1 in $10^{+10}$, and the transduction frequency of a functional arg marker is greater than the reversion frequency.

Another aspect of the present invention is directed to a method of producing a product or an intermediate of a metabolic pathway from a microbe. Preferably, the method produces a secondary metabolite. Preferably, the donor and recipient are Actinomycetales, more preferably a Streptomycetaceae, most preferably a Streptomyces.

The method of producing a product or an intermediate of a metabolic pathway, preferably a secondary metabolite, from a microbe is similar to the method of transferring at least one nucleic acid fragment from a donor microbe to a recipient microbe, as described herein. When producing a secondary metabolite, the method can include providing conditions effective for the recipient microbe to produce the secondary metabolite. The secondary metabolite produced by the transduced recipient can be produced by the donor. The secondary metabolite produced by the transduced recipient microbe can be produced by the recipient microbe prior to transduction. Preferably, if the secondary metabolite is the same as one produced by the donor or recipient microbe prior to transduction, the transduced recipient produces a secondary metabolite at a higher level than is produced by the donor microbe or the recipient microbe prior to transduction.

Alternatively and significantly, it is anticipated that the methods of the present invention will allow for the production of secondary metabolites that are not produced by the recipient microbe prior to transduction or by the donor microbe, i.e., new secondary metabolites. New secondary metabolites are often referred to in the art as new natural products, or non-natural products. The concept of the production of secondary metabolites that are not produced by the recipient microbe prior to transduction or by the donor microbe is typically referred to in the art as combinatorial biosynthesis.

The present invention is illustrated by the following examples. It is to be understood that the particular examples, materials, amounts, and procedures are to be interpreted broadly in accordance with the scope and spirit of the invention as set forth herein.

EXAMPLES

These examples detail the isolation of the first generalized transducing phages for *Streptomyces coelicolor*, the most genetically well characterized strain of m this important bacterial genus. Phages ranging in size from approximately 25 kb to more than 60 kb were shown to transduce a number of markers at frequencies from $10^{-5}$ to $10^{-8}$. Transduction is apparently general since markers were transduced from locations around the entire chromosome. Co-transduction of several markers predicts linkage that is in good agreement with data obtained from genetic mapping by conjugal mating. An important aspect of the invention was the establishment of conditions that severely reduce superinfection killing during selection of transductants. It is expected that generalized transduction will provide an important genetic tool for the study and manipulation of this organism.

*Streptomyces coelicolor* phages DAHH DAH5 and DAH6 (AATC Accession Numbers 203877, 203879, respectively) and *Streptomyces avermitilis* phages JSN1, JSN2, and JSN3 (ATCC Accession Numbers 203874, 203875, and 203876, respectively were deposited with the American Type Culture Collection, 10801 University Blvd., Manassas, Va., 20110-2209, USA, on Mar. 25, 1999. The deposits were made under the Budapest Treaty on the International Recognition of the Deposit of Microorganisms for the Purposes of Patent Procedure.

Example 1

Experimental Procedures

Bacterial strains and culture conditions. Bacterial strains used in this study are listed in Table 1. Spore stocks were made from strains grown on MYM (Brawner et al., (1985) *Gene*, 40, 191–201). To prepare spore stocks, bacteria were streaked for isolated colonies on MYM media and incubated and 30° C. for 4 days. An isolated colony was picked and spread on MYM plates and incubated at 30° C. for 4 days or until spores were visible. The spores were removed with a cotton swab and stored at −20° C. Antibiotics used in the experiments described herein and the concentrations are listed in Table 2.

TABLE 1

Bacterial Strains and Culture Conditions

| SPECIES | STRAIN | GENOTYPE | SOURCE |
|---|---|---|---|
| Streptomyces coelicolor | A3(2) | WT | John Innes Centre Norwich, UK |
| Streptomyces coelicolor | J2402 | M145, prototrophic SCP1⁻ SCP2⁻ whiB::hyg | K Chater John Innes Centre Norwich, UK |
| Streptomyces coelicolor | J1258 | proAl hisC9 argAl cysDl8 uraAl strAl | K. Chater John Innes Centre Norwich, UK |
| Streptomyces coelicolor | J2408 | M145, prototrophic SCP1⁻ SCP2⁻ whiH::ermE | K. Chater John Innes Centre Norwich, UK |
| Streptomyces coelicolor | YU105 | proAl argAl redE60 act::ermE whiE::hyg | J. Nodwell McMaster University Hamilton, Ontario |
| Streptomyces coelicolor | BldK::Ω | bldK::str/spc | J. Nodwell McMaster University Hamilton, Ontario |
| Streptomyces coelicolor | J222 | uraAl rifAl | K. Chater John Innes Centre Norwich, UK |
| Streptomyces coelicolor | J2709 | proAl hisC9 argAl uraAl | K. Chater John Innes Centre Norwich, UK |
| Streptomyces coelicolor | J1258 | proAl hisC9 argAl cysDl8 utaAl strAl NF | |
| Streptomyces lividans | 1326 | WT | John Innes Centre Norwich, UK |
| Streptomyces lividans | TK64 | proAl | John Innes Centre Norwich, UK |
| Streptomyces venezuelae | 10712 | WT | C. Stuttard Dalhousie University Halifax, NS, Canada |
| Streptomyces venezuelae | JW1100 | pdx | C. Stuttard Dalhousie University Halifax, NS, Canada |
| Streptomyces venezuelae | JW1400 | rib | J. Westpheling Athens, GA |
| Streptomyces avermitilis | 32172 | WT | C. Denoya Prizer Groton, CT |
| Streptomyces avermitilis | CD1251 | ermE | C. Denoya Pfizer Groton, CT |
| Sacchatopolyspora erythraea | 2338 | WT | C. Denoya Pfizer Groton, CT |

TABLE 2

Antibiotics

| STRAIN | ANTIBIOTIC | CONCENTRATION |
|---|---|---|
| J222 | Rifampicin | 50 µg/ml |
| J2402 | Hygromycin | 100 µg/ml |
| J2408 | Lincomycin | 150 µg/ml |
| | Erythromycin | 75 µg/ml |
| YU015 | Hygromycin | 100 µg/ml |
| | Lincomycin | 150 µg/ml |
| | Erythromycin | 75 µg/ml |
| CD1251 | Erythromycin | 5 µg/ml |
| BldK::Ω | Spectinomycin | 50 µg/ml |
| J1258 | Streptomycin | 15 µg/ml |

Isolation of phage. Approximately 25 grams of top soil, collected in plastic vials, was incubated with 15 mls of Actinomycete Phage Buffer (APB, 4 mM Ca(NO$_3$)$_2$, 10 mM Tris HCL, 0.005% gelatin) (Vats, S. et al., (1987) *J. Bacteriol.* 169, 3809–3813) overnight at room temperature on a rocking shaker. The mixture was centrifuged at 3,000 rpm for 10 minutes and the supernatant was passed through a 0.45 µm cellulose acetate filter (Nalgene, Rochester, N.Y.). The phage-containing filtrate was stored at 4° C. To detect phage, 100 µl of filtrate was added to *Strepioniyces coelicolor* spores diluted to approximately $10^7$ cfu/ml. Cfu refers to colony forming unit. The mixture was added to 4 ml of Nutrient Soy (Difco, Detroit, Mich.) (Nutrient Soy contains 0.3% beef extract, 0.5% peptone) and 0.7% agar (NSA, also referred to as "top agar") and poured over Nutrient Agar (Difco, Detroit, Mich.) plates (Nutrient Agar contains 0.3% beef extract and 0.5% peptone) and 1.5% agar, 4 mM $Ca(NO_3)_2$, and 0.5% Dextrose (referred to as "NCG plates"). Agar was obtained from Difco. Plates were incubated at 25° C. for 3 days and examined for turbid plaques.

Phage were isolated by three rounds of plaque purification. From the top agar individual plaques were picked with a toothpick and streaked onto a lawn of spores ($10^7$ cfu) that had been spread on Nutrient Agar. The plates were incubated at 25° C. for 3 days. This process was repeated twice to generate a lawn of isogenic plaque-purified phage. A starter lysate was made by adding 2 ml of APB to the lawn of plaque-purified phage. A sterile glass rod was used to scrape the top agar from the underlying agar plate which was then transferred to a sterile centrifuge tube, vortexed, and centrifuged at 10,000 RPM for 10 minutes to clarify lysate from cell debris. The phage-containing supernatant (lysate) was then transferred to a sterile tube and stored at 4° C.

Preparation of phage stocks. Phages were propagated on donor strains by standard agar-layer techniques (Sambrook, (1989) *Moleciilar Cloning: A Labotratory Manual*, 2nd Ed., Cold Spring Harbor Laboratory Press, p. 2.65) with APB used as phage diluent. The phage stocks were prepared by adding 100 µl of the starter lysate to $10^7$ cfu spores of the appropriate donor strain. This mixture was then added to 4 ml of NSA and poured over NCG plates. A total of 10 plates per phage were made. The plates were incubated at 25° C. for 5 days. The phage lawns were harvested by adding 2 ml of APB to the first plate only of each phage 10 plate set, and the NSA transferred to the next plate. This process was repeated with the top agar transferred from plate to plate in series. The phage lawns from all 10 plates were then transferred to a centrifuge tube, vortexed, and centrifuged as above. Phage lysates were purified by filtration through a 0.45 Nalgene cellulose acetate filter. Each phage lysate was titered (i.e., the number of phage determined) by diluting the phage in APB and spotting 20 µl of each dilution onto lawns ($10^7$ cfu) of spores on NSA. The "titer" of a lysate is the number of plaque forming units (pfu) per ml of lysate.

Preparation of germlings. Spores were incubated at 50° C. for 10 minutes in 0.05 M TES buffer (TES: N-tris (Hydroxymethyl)methyl-2-aminoethanesulfonic acid), pH 7.2 (Hopwood, et al., (1985) *Genetic Manipulation of Sfreptomyces—A Laboratory Manual*, The John Innes Foundation, Norwich, UK, pp. 8–9). An equal volume of 2×germination broth (GB) (2×GB: 1% yeast extract, 1% casaminoacids, and 0.01M $CaCl_2$) was added, and the germlings were incubated at 30° C. for 2 hours, centrifuged for 5 minutes at 6,000 rpm and resuspended in water. At 2 hours, a sample is removed and examined using a light microscope to determine if the spores are beginning germination. The appearance of germ tubes from the spores indicates germination. The culture is considered germlings when about 80% of the spores show short germ tubes.

Adsorption assay. Germlings were prepared as described above. At 2 hours, the germlings were centrifuged and resuspended in MYM broth, and incubated at 30° C. for an additional 4 hours. A 100 µl sample of germlings (about $10^5$) was taken once each hour from 0 to 6 hours. The germling samples were added to phage (at a concentration of $10^5$ pfu/ml) and incubated for 30 minutes at room temperature to allow for adsorption. Each mixture was then centrifuged for 5 minutes at 10,000 rpm to pellet germlings and any adsorbed phages. The titer of free phage remaining in the supernatant was determined by diluting the supernatant in APB and spotting 20 µl of each dilution onto a lawn of about $10^7$ spores on NSA.

UV irradiation. A kill curve was established for each phage by exposing phage suspended in APB ($10^6$ pfu/ml) to ultraviolet (UV) light (250–260 nm) at an intensity of 2 $mW/cm^2/s$ and sampling at 10 seconds, 20 seconds, and 30 seconds. The samples containing the phage were approximately 6 inches from the UV light (Sylvania, Danners, Mass.). Phage were subsequently diluted in APB, and phage titers were determined by spotting 20 µl of each dilution onto a lawn of $10^7$ so coelicolor A3 (2) spores on NSA as described herein.

Inactivation of phage with citrate. To determine phage sensitivity to sodium citrate, phage was diluted in APB and titered by spotting 20 µl of each dilution onto a lawn of $10^7$ *Streptomyces coelicolor* spores on NSA containing 10 mM sodium citrate. Plates were incubated at either 22° C. or 30° C. for 3 days and examined for plaques.

Genetic transduction assays. High titer (approximately $10^{10}$ pfu/ml) phage lysates were prepared on donor strains as described herein (see Preparation of phage stocks), added to recipient germlings and incubated at room temperature for 30 minutes, then spread on supplemented minimal glucose medium (Hopwood, et al., (1985) *Genetic Manipulation of Streptomyces—A Laboratory Manual*, The John Innes Foundation, Norwich, UK, p. 223) or NCG containing antibiotic and incubated at for 5–7 days 22° C. Minimal glucose medium was supplemented with 0.02% trace elements solution. Trace elements solution (100%) contains 0.004% $ZnCl_2$, 0.02% $FeCl_3$, 0.001% $CuCl_2$, 0.001% $MgCl_2$, 0.001% $Na_2B_4O_7$, and 0.001% $(NH_4)_6Mo_4O_{24}$ (Hopwood, et al., (1985) *Genetic Manipulation of Streptomyces—A Laboratory Manual*, The John Innes Foundation, Norwich, UK, p. 235).

Transduction frequencies were calculated as the number of colonies obtained after incubation for 5–7 days per pfu added to the recipient strain. To prevent superinfection killing, the phage were either irradiated with UV to 0.1% survival using the established kill curve described herein prior to their addition to germlings, or the phage-germlings mixture was plated on medium that contained 10 mM sodium citrate.

Southern hybridization analysis. Chromosomal DNA is purified from Streptomyces using the protocol for rapid small scale isolation of total DNA (Hopwood, et al., (1985) *Genetic Manipulation of Streplomyces—A Laboratory Manual*, The John Innes Foundation, Norwich, UK, pp. 72–74) Briefly, total DNA is isolated as follows. A single colony is picked and used to in oculate 50 ml of YEME broth (0.3% yeast extract, 0.5% bacto peptone, 0.3% malt extract, 1% dextrose, 34% sucrose, and 5 mM $MgCl_2$) which is then incubated 30° C. for 40 hours. The cells are harvested by centrifugation at 6,000 rpm for 10 minutes. The resulting pellet is then resuspended in 5 ml of SET buffer (75 mM NaCl, 25 mM EDTA, pH 8.0, and 20 mM Tris pH 7.5). Lysozyrne (1 mg/ml final concentration), is added to the pellet suspension and incubated at 37° C. for 1 hour, at which time Proteinase K (final concentration 56 µg/ml) and sodium dodecyl sulfate (SDS, final concentration 1%,) is added to the suspension and incubated at 55° C. for 2 hours. After incubation, NaCl (final concentration 0.8 M) is added. The resulting mixture is then extracted once with an equal volume of phenol and once with an equal volume of a 1:1 mixture of phenol/chloroform. To the aqueous phase, Proteinase K (final concentration 1.5 mg/ml) and 500 mg of sarkosyl are added and the aqueous phase is incubated overnight at 37° C. The solution is then extracted again with an equal volume of a 1:1 mixture of phenol/chloroform, and then again with an equal volume of chloroform. Next, to precipitate the DNA, 0.1 volume of 3 M sodium acetate and 0.6 volume of 2-propanol are added. The DNA can then be spooled onto a sterile glass rod and suspended in about 1 ml of 10 mM Tris, pH 8.0. The DNA is stored at 4° C.

Genomic DNA is digested with the restriction enzymes DraI and AseI (Boehringer Mannheim, Indianapolis, Ind.) following the manufacturer's instructions. The resulting DNA fragments are separated by electrophoresis on a 0.8% agarose gel. The resolved DNA fragments are transferred to a nitrocellulose membrane using technics well known to the art (Sambrook, (1989) Molecular Cloning: A Laboratory Manual, 2nd Ed., Cold Spring Harbor Laboratory Press, pp. 9.31–9.55). Southern hybridizations use either a hygB gene probe or an ermE gene probe.

The hygB gene is isolated from pUH19b (obtained from Richard Seyler, University of Georgia) by cutting the plasmid with NcoI (New England BioLabs, Beverly, Mass.) liberating a fragment containing the hygB gene. The fragment is gel-purified by separation by electrophoresis on 0.8% agarose gel. The hygB fragment (determined by size) is cut out of the gel, and the DNA eluted using a Promega (Madison, Wis.) Wizard DNA Purification System. An ermE gene probe is obtained and used in Southern hybridization analysis.

The probes are labeled at the 5' end with [$\alpha$-$^{32}$P] dATP using techniques well known to the art. Prehybridization and hybridization buffers consist of the following (final concentrations given): 6×SSC (1×SSC is 0.15 M NaCl, 0.015 M sodium citrate), 5×Denhardt's solution (50×Denhardt's: 10 grams/liter Ficoll Type 400, 10 grams/liter polyvinylpyrrolidone, 10 grams/liter bovine serum albumin Fraction V), 0.1% SDS, 10 mM potassium phosphate, pH 7.2, and 250 mg/ml salmon sperm DNA. Prehybridization is for 2 hours at 55° C., and hybridization is overnight at 55° C. with about 50 pmol of radiolabelled probe. Hybridization is followed by 3 consecutive washes at room temperature for 15 minutes each in a solution containing 2×SSC and 0.1% SDS, followed by 3 consecutive washes at 37° C. for 15 minutes each in a solution containing 1×SSC and 0.1% SDS. Kodak X-Ohiat scientific imaging film is used for autoradiography.

Phage DNA isolation and characterization. Phage DNA was prepared by the method of Hopwood, et al., ((1985) *Genetic Manipulation of streptomyces—A Laboratory Manual*, The John Innes Foundation, Norwich, UK, pp 99–102) with the following modifications. Lysates were centrifuged at 25,000 rpm for 90 minutes at 4° C. to sediment phage. Phage pellets were resuspended in RNAase solution (50 µg/ml in APB, the RNAse was obtained from Sigma (St. Louis, Mo.)), incubated at 37° C. for 20 minutes followed by the addition of 80 µl of a 10% SDS solution and incubation at 70° C. for 30 minutes. One hundred µl of 8 M ammonium acetate was added and the mixture was incubated for 15 minutes on ice, then centrifuged 10 minutes at 4° C. The supernatant was extracted with phenol, (1 volume supernatant: 1 volume phenol), extracted with 1 phenol: 1 chloroform (1 volume supernatant: 1 volume phenol:chloroform), and extracted with chloroform (1 volume supernatant: 1 volume chloroform). The nucleic acid was precipitated with ethanol. Digestion of DNA with for instance BamHI, DraI, AseI, EcoRV, and ScpII (Boehringer Mannheim, Indianapolis, Ind.) was carried out following the manufacturers instructions and separated on 0.8% agarose gel.

Results

Most wild type phage isolated from soil were found to be temperature sensitive for lytic growth on *Streptomyces coelicolor*. Twenty-six soil samples from ten different locations around Athens, Georgia were collected and extracted with phage buffer. Samples of the extracts were tested for the presence of plaque forming units at 30° C. Nine phages, assumed to be different from each other because of differences in plaque morphology, were purified. All nine phages formed turbid plaques and yielded lower titer lysates ($10^5$ to $10^7$) as compared to the same phage grown at 30° C. which formed clear, large plaques and yielded higher titer lysates ($10^8$ to $10^{10}$). The turbidity of a turbid plaque was due to cells within the plaque that arc not lysed by other phage in the plaque. It was distinguished from other clear plaques (plaques in which all the bacteria in the region are killed and lysed) because of the turbid center. A comparison of phage titers generated from *Streptomyces coelicolor* at 22° C. and 30° C. (Table 3) indicates that the phage are naturally temperature sensitive for lytic growth.

TABLE 3

Temperature Sensitivity of Phage Isolated from Soil. The titer of each phage was determined at 22° C. and 30° C. in the presence and absence of citrate.

| Phage | 22° C. − Citrate | 22° C. + Citrate | 30° C. − Citrate | 30° C. + Citrate |
| --- | --- | --- | --- | --- |
| DAH1 | $1 \times 10^5$ Turbid plaques | 0 | $2.5 \times 10^7$ Clear plaques | 500 Turbid plaques |
| DAH2 | $3 \times 10^6$ Turbid plaques | 10 Turbid plaques | $2.5 \times 10^7$ Clear plaques | $4 \times 10^5$ Turbid plaques |
| DAH3 | $5 \times 10^6$ Turbid plaques | 300 Turbid plaques | $1.5 \times 10^9$ Clear plaques | $5 \times 10^7$ Turbid plaques |
| DAH4 | $2.5 \times 10^7$ Turbid plaques | 400 Turbid plaques | $5 \times 10^9$ Clear plaques | $5 \times 10^6$ Turbid plaques |
| DAH5 | $1 \times 10^5$ Turbid plaques | 30 Turbid plaques | $4 \times 10^7$ Clear plaques | $5 \times 10^3$ Turbid plaques |
| DAH6 | $1 \times 10^5$ Turbid plaques | 75 Turbid plaques | $1 \times 10^6$ Clear plaques | $5 \times 10^3$ Turbid plaques |

Phage inactivation reduces superinfection killing. The release of large numbers of phage from infected cells during growth leads to superinfection. Superinfection refers to a recipient containing a nucleic acid fragment from a phage particle and a nucleic acid fragment from a transducing particle. Superinfection typically leads to the killing of transductants. This is referred to as superinfection killing and the amount of superinfection killing that occurs has a dramatic effect on the number of transductants recovered. To reduce.superinfection killing of transductants, several methods were investigated to inhibit phage infection.

As shown in FIG. 1, exposure of the phage particles to UV light resulted in a sharp decrease in phage titer. All of the Streptomyces phages tested were sensitive to inactivation by UV at doses and times similar to those used for mutagenesis of phage P1. While UV light was effective at preventing phage infection, its potential mutagenic effects on DNA within transducing particles made it a less than desirable method for phage killing.

Citrate is a chelator of divalent metal ions and has been shown to prevent phage adsorption at concentrations that do not affect the growth of bacterial cells (Vats, S. et al., (1987) *J. Bacteriol.* 169, 3809–3813). To test for sensitivity to citrate, phage were titered on NCG plates with and without sodium citrate. No plaque forming units were visible after 1 day at 22° C. Three days after plating, small, turbid plaques ($10^2$) were visible indicating some phage adsorption. However, the number of plaques is significantly less than on control plates without citrate. Dilutions of cells plated on the same medium showed no effect on the viability of *Streptomyces coelicolor*.

Genetic transduction in *Streptoniyces coelicolor* is efficient and generalized. Each newly isolated phage was examined for its ability to mediate transduction. Transduction assays were performed at 22° C. to reduce lytic growth of the phage. To reduce superinfection, two different methods were used: 1) the phage were irradiated prior to addition to germlings; or 2) the phage-germling mixture was plated on medium containing 10 mM sodium citrate. Transduction of several auxotrophic and drug resistance markers in *Streptomyces coelicolor* was examined for each phage. Surprisingly and unexpectedly, transduction of several markers at frequencies ranging from $10^{-4}$ to $10^{-8}$ cfu/pfu was detected (Table 4). The markers transduced are positioned around the entire chromosome and the frequencies of transduction are similar suggesting that transduction is generalized. Transduction is efficient as the transduction frequencies are at least 3 orders of magnitude higher that the reversion frequency of the recipient strain (see Table). Also, these frequencies are well within the range of frequencies reported for other transducing phages. For example, P22 (a well established transducing phage of Salmonella) transduces markers at frequencies ranging $10^{-4}$ to $10^{-8}$.

The ability of phage to mediate transduction was determined in other Streptomyces spp. (*Streptomyces avermitilis, Streptomyces lividans,* and *Streptomyces venezuelae*). Surprisingly and unexpectedly, intraspecific transduction was observed at frequencies of about $10^{-5}$ for *Streptomyces avermitilis*, about $10^{-4}$ to about $10^{-6}$ for *Streptomyces lividans*, and about $10^{-6}$ to about $10^{-8}$ for *Streptotnyces venezieelae*. Particularly surprising was the observed intergeneric transduction between *Saccharopolyspora erythraea* and *Streptoinyces avermitilis* (Table 4).

In Table 4, the germling only control is the recipient with no phage added. This control indicates the reversion frequency of the strain, i.e., how often one would expect to see spontaneous revertants. The phage only control is the phage with no recipient strain added. This is a test for contamination of phage lysates.

Auxotrophic markers: proA1 means that the recipient strain cannot grow unless the media is supplemented with proline or a transducing phage provided the recipient cell with the appropriate gene from the donor strain. This is true for hisC9, argA1, and uraA1 as well; recipient will not grow without supplemented histidine, arginine, or uracil unless the phage provided the cell with the appropriate genes from the donor strain.

Antibiotic resistance: rifA1 means that the strain is resistant to rifampicin and therefore, will grow in the presence of rifampicin. Strains without a rifA1 genotype are sensitive to rifampicin and can only grow if a transducing phage has provided the appropriate gene from the donor strain. This is the same for all antibiotic markers. strA confers resistance to streptomycin, hygB confers resistance to hygromycin and ermE confers resistance to erythromycin and lincomycin.

TABLE 4

Transduction

| DONOR STRAIN | PHAGE | RECIPIENT STRAIN | SELECTED MARKER | RECIPIENT STRAIN REVERSION FREQUENCY | TRANSDUCTION FREQUENCY |
|---|---|---|---|---|---|
| A. Intraspecific Transduction *Streptomyces coelicolor* | | | | | |
| J222, uraAl rifAl NF | DAH2 | J2799, pro his arg cys ura | Arginine + | | $3 \times 10^{-7}$ |
| J222, uraAl rifAl NF | DAH2 | | Arginine + | | 0 |
| J222, uraAl rifAl NF | DAH4 | J2709, pro his arg cys ura | Arginine + | | $3 \times 10^{-6}$ |
| J222, uraAl rifAl NF | DAH4 | | Arginine + | | 0 |
| J222, uraAl rifAl NF | DAH5 | J2709, pro his arg cys ura | Arginine + | | $3 \times 10^{-6}$ |
| J222, uraAl rifAl NF | DAH5 | | Arginine + | | 0 |
| J222, uraAl rifAl NF | DAH6 | J2709, pro his arg cys ura | Arginine + | | $5 \times 10^{-6}$ |
| J222, uraAl rifAl NF | DAH6 | | Arginine + | | 0 |
| | | J2709, pro his arg cys ura | Arginine + | <1 in $10^{+10}$ | |
| J222, uraAl rifAl NF | DAH2 | J2709, pro his arg cys ura | Histidine + | | $8 \times 10^{-7}$ |
| J222, uraAl rifAl NF | DAH2 | | Histidine + | | 0 |
| J222, uraAl rifAl NF | DAH4 | J2709, pro his arg cys ura | Histidine + | | $5 \times 10^{-5}$ |
| J222, uraAl rifAl NF | DAH4 | | Histidine + | | 0 |
| J222, uraAl rifAl NF | DAH5 | J2709, pro his arg cys ura | Histidine + | | $3 \times 10^{-7}$ |
| J222, uraAl rifAl NF | DAH5 | | Histidine + | | 0 |
| J222, uraAl rifAl NF | DAH6 | J2709, pro his arg cys ura | Histidine + | | $7 \times 10^{-6}$ |
| J222, uraAl rifAl NF | DAH6 | | Histidine + | | 0 |
| | | J2709, pro his arg cys ura | Histidine + | <1 in $10^{+10}$ | |
| J222, uraAl rifAl NF | DAH2 | J2709, pro his arg cys ura | Proline + | | $3 \times 10^{-6}$ |
| J222, uraAl rifAl NF | DAH2 | | Proline + | | 0 |
| J222, uraAl rifAl NF | DAH4 | J2709, pro his arg cys ura | Proline + | | $3 \times 10^{-6}$ |
| J222, uraAl rifAl NF | DAH4 | | Proline + | | 0 |

TABLE 4-continued

Transduction

| DONOR STRAIN | PHAGE | RECIPIENT STRAIN | SELECTED MARKER | RECIPIENT STRAIN REVERSION FREQUENCY | TRANSDUCTION FREQUENCY |
|---|---|---|---|---|---|
| J222, uraAl rifAl NF | DAH5 | J2709, pro his arg cys ura | Proline + | | $7 \times 10^{-6}$ |
| J222, uraAl rifAl NF | DAH5 | | Proline + | | 0 |
| J222, uraAl rifAl NF | DAH6 | J2709, pro his arg cys ura | Proline + | | $5 \times 10^{-6}$ |
| J222, uraAl rifAl NF | DAH6 | | Proline + | | 0 |
| | | J2709, pro his arg cys ura | Proline + | <1 in $10^{+10}$ | |
| J222, uraAl rifAl NF | DAH2 | A3(2), WT | Rifampicin resistance | | $5 \times 10^{-6}$ |
| J222, uraAl rifAl NF | DAH2 | | Rifampicin resistance | | 0 |
| J222, uraAl rifAl NF | DAH4 | A3(2), WT | Rifampicin resistance | | $3 \times 10^{-6}$ |
| J222, uraAl rifAl NF | DAH4 | | Rifampicin resistance | | 0 |
| J222, uraAl rifAl NF | DAH5 | A3(2), WT | Rifampicin resistance | | $7 \times 10^{-6}$ |
| J222, uraAl rifAl NF | DAH5 | | Rifampicin resistance | | 0 |
| J222, uraAl rifAl NF | DAH6 | A3(2), WT | Rifampicin resistance | | $5 \times 10^{-6}$ |
| J222, uraAl rifAl NF | DAH6 | | Rifampicin resistance | | 0 |
| | | A3(2), WT | Rifampicin resistance | <1 in $10^{+10}$ | |
| *Streptomyces avermitilis* | | | | | |
| CD1251 | JSN | 31272, WT | Lincomycin resistance | | $4 \times 10^{-5}$ |
| CD1251 | JSN | | Lincomycin resistance | | 0 |
| CD1251 | JSN3 | 31272, WT | Lincomycin resistance | | $3 \times 10^{-5}$ |
| CD1251 | JSN3 | | Lincomycin resistance | | 0 |
| | | 31272, WT | Lincomycin resistance | <1 in $10^{+9}$ | |
| *Streptomyces venezuelae* | | | | | |
| 10712, WT | SV1 | JW1400, rib | Riboflavin + | | 0 |
| 10712, WT | SV1 | | Riboflavin + | | 0 |
| 10712, WT | BTH | JW1400, rib | Riboflavin + | | 0 |
| 10712, WT | BTH | | Riboflavin + | | 0 |
| 10712, WT | MRT | JW1400, rib | Riboflavin + | | $7 \times 10^{-8}$ |
| 10712, WT | MRT | | Riboflavin + | | 0 |
| | | JW1400, rib | Riboflavin + | <1 in $10^{+10}$ | |
| 10712, WT | SV1 | JW1100, pdx | Pyridoxal + | | 0 |
| 10712, WT | SV1 | | Pyridoxal + | | 0 |
| 10712, WT | BTH | JW1100, pdx | Pyridoxal + | | $2.5 \times 10^{-8}$ |
| 10712, WT | BTH | | Pyridoxal + | | 0 |
| 10712, WT | MRT | JW1100, pdx | Pyridoxal + | | $2 \times 10^{-6}$ |
| 10712, WT | MRT | | Pyridoxal + | | 0 |
| | | JW1100, pdx | Pyridoxal + | <1 in $10^{+10}$ | |
| *Streptomyces lividans* | | | | | |
| 1326, WT | DAH2 | TK64 | Proline + | | $3 \times 10^{-6}$ |
| 1326, WT | DAH2 | | Proline + | | 0 |
| 1326, WT | DAH3 | TK64 | Proline + | | $2 \times 10^{-5}$ |
| 1326, WT | DAH3 | | Proline + | | 0 |
| 1326, WT | DAH4 | TK64 | Proline + | | $4 \times 10^{-5}$ |
| 1326, WT | DAH4 | | Proline + | | 0 |
| 1326, WT | DAH5 | TK64 | Proline + | | $1 \times 10^{-6}$ |
| 1326, WT | DAH5 | | Proline + | | 0 |
| 1326, WT | DAH6 | TK64 | Proline + | | $1 \times 10^{-6}$ |
| 1326, WT | DAH6 | | Proline + | | 0 |
| | | TK64 | Proline + | <1 in $10^{+10}$ | |
| B. Interspecific Transduction | | | | | |
| *Saccharopolyspora erythraea*, WT | JSN1 | 31272, WT | Lincomycin resistance | | $4 \times 10^{-4}$ |
| *Saccharopolyspora erythraea*, WT | JSN1 | | Lincomycin resistance | | 0 |
| *Saccharopolyspora erythraea*, WT | JSN2 | 31272, WT | Lincomycin resistance | | $3 \times 10^{-6}$ |

TABLE 4-continued

Transduction

| DONOR STRAIN | PHAGE | RECIPIENT STRAIN | SELECTED MARKER | RECIPIENT STRAIN REVERSION FREQUENCY | TRANSDUCTION FREQUENCY |
|---|---|---|---|---|---|
| Saccharopolyspora erythraea, WT | JSN2 | | Lincomycin resistance | | 0 |
| Saccharopolyspora erythraea, WT | JSN3 | 31272, WT | Lincomycin resistance | | $4 \times 10^{-4}$ |
| Saccharopolyspora erythraea, WT | JSN3 | | Lincomycin resistance | | 0 |
| | | 31272, WT | Lincomycin resistance | <1 in $10^{+9}$ | |

Co-transduction confirms linkage established by conjugal mating for several genetic markers. To examine co-transduction (i.e., the transfer of two genetic markers at the same time) of markers by these phage, genes identified by mutations that had been previously mapped using conjugal imitating or physical mapping were used in combination with each other and with drug resistance markers that had been introduced into known locations within the chromosome. As shown in Table 5, co-transduction was observed at frequencies that are in good agreement with previously reported linkage.

strongly suggests that the phage provide the recipient cells with the gene that confers resistance to hygromycin from the donor strain. To confirm that the transductants contained the transferred drug resistance gene, DNAs isolated from randomly selected transductants are analyzed by Southern blotting using the hygB drug resistance gene probe. DNA hybridization patterns of the transductants is the same as those of the donor strain, while no hybridization is seen with the recipient strain. A gene probe for the ermE gene present in the recipient strain hybridizes with the DNA from the transductants, but does not hybridize with the donor strain.

TABLE 5

Cotransduction

| DONOR STRAIN | PHAGE | RECIPIENT STRAIN | SELECTED MARKER | RECIPIENT STRAIN REVERSION FREQUENCY | TRANSDUCTION FREQUENCY | SCREENED MARKER | COTRANSDUCTION FREQUENCY |
|---|---|---|---|---|---|---|---|
| YU105, pro arg red act::ermE whiE::hyg | DAH5 | bldK::Ω | Lincomycin resistance | | $2 \times 10^{-8}$ | Spectinomycin sensitivity | 100% |
| YU105, pro arg red act::ermE whiE::hyg | DAH5 | | Lincomycin resistance | | 0 | | |
| YU105, pro arg red act::ermE whiE::hyg | DAH6 | bldK::Ω | Lincomycin resistance | | $3 \times 10^{-8}$ | Spectinomycin sensitivity | 100% |
| YU105, pro arg red act::ermE whiE::hyg | DAH6 | | Lincomycin resistance | | 0 | | |
| | | bldK:Ω | Lincomycin resistance | <1 in $10^{+9}$ | | | |
| argA1 cysD18 uraA1 straA1 NF | DAH5 | J222 | Streptomycin resistance | | $2 \times 10^{-6}$ | Rifampicin sensitivity | 50% |
| argA1 cysD18 uraA1 straA1 NF | DAH5 | | Streptomycin resistance | | 0 | | |
| argA1 cysD18 uraA1 straA1 NF | DAH6 | J222 | Streptomycin resistance | | $1 \times 10^{-5}$ | Rifampicin sensitivity | 100% |
| argA1 cysD18 uraA1 straA1 NF | DAH6 | | Streptomycin resistance | | 0 | | |
| | | J222 | Streptomycin resistance | <1 in $10^{+9}$ | | | |

Physical analysis of transductants confirms DNA transfer. To examine the physical location of transduced markers in the recipient chromosome, Southern hybridization experiments are performed. DNA is isolated from S. coelicolor strains J2402, which contains a hygB insertion into the whiB gene, and J2408, which contains an ermE insertion into the whiH gene. Phage grown on strain J2402 is added to J2408 germlings, and cells that are resistant to both hygromycin (encoded by hygB) and lincomycin (encoded by ermE) are isolated from cultures at a frequency above the reversion frequency. No doubly resistant cells are recovered from control cultures (no phage added) in any experiment, which These experiments demonstrate that chromosomal DNA from the donor strain is transferred by the phage to the transductant strain and integrated in the host chromosome.

Transduction was not detected when assays were performed at 30° C. These phages were exceptional in their ability to grow lytically at 30° C., the growth temperature typically used to incubate S. coelicolor and in fact most streptomycete strains. If lawns with only a few plaques were incubated at 30° C., the entire lawn was lysed in a few days. Extensive superinfection killing resulting from this active lytic growth might explain the failure to detect transduction in many Streptomyces species. In fact, when transduction assays were performed exactly as described above but at 30° C., no transductants were detected. It is very likely that superinfection killing does, in fact, reduce or eliminate the ability of transductants to survive.

Preliminary physical characterization of the transducing phages reveals that they are different from each other. To determine the size of the phage genomes, nucleic acid was extracted from four phage, DAH2, DAH4, DAH5, and DAH6, using a standard approach for Streptomyces phages (Hopwood, et al., (1985) *Genetic Manipulation of Streptomyces—A Laboratory Manual*, The John Innes Foundation, Norwich, UK, pp. 99–102). In all cases the nucleic acid isolated from the phages was digested with several restriction enzymes thus indicating that it is double stranded DNA. The genome sizes were estimated using digestion with restriction endonucleases and separation of fragments by agarose gel electrophoresis. The size of DNA isolated from DAH2, DAH4, DAH5, and DAH6 was about 60 kilobases (kb), 45 kb, 45 kb, and 25 kb, respectively. The differences in size strongly suggest that there are at least three different types of phage. Moreover, the differences in transduction frequencies and the differences in plaque morphology between DAH4 and DAH5 strongly suggest that these two phages are not the same phage, despite the similar size of the DNA. Thus, DAH2, DAH4, DAH5, and DAH6 are each unique.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations, of this invention will become apparent to those skilled in the art without departing from the scope and spirit of this invention, and it should be understood that this invention is not to be unduly limited to the illustrative embodiments set forth herein.

What is claimed is:

1. A method of producing a transducing particle, the method comprising:
    combining an isolated transducing phage with a donor Actinomycetales microbe to form a phage-donor microbe mixture, wherein the isolated transducing phage can transfer at least one nucleic acid fragment from a donor Actinomycetales microbe to a recipient Actinomycetales microbe at a temperature of less than 28° C., wherein the frequency of transduction is at least $10^{-5}$; and
    incubating the phage-donor microbe mixture to produce a transducing particle.
2. The method of claim 1 wherein the at least one nucleic acid fragment comprises a nucleic acid fragment selected from the group consisting of at least one non-coding region and at least one coding region or a portion thereof.
3. The method of claim 1 wherein the donor Actinomycetales and the recipient Actinomycetales are selected from the group consisting of spores, mycelial fragments, germlings, protoplasts, and mixtures thereof.
4. The method of claim 1 wherein the Actinomycetales is a Streptomycetaceae.
5. The method of claim 4 wherein the Streptomycetaceae is a Streptomyces.
6. The method of claim 1 wherein the donor microbe and the recipient microbe are members of different genera.
7. The method of claim 1 wherein the donor microbe and the recipient microbe are members of different species.
8. The method of claim 1 wherein the donor microbe and the recipient microbe are members of the same species.
9. The method of claim 1 further comprising isolating the transducing particle.
10. A transducing particle isolated by the method of claim 9.
11. A transducing phage isolated by a method comprising:
    combining a phage with a donor Actinomycetales microbe to form a first mixture and incubating the first mixture under conditions such that a lysate is produced;
    combining the lysate with a recipient Actinomycetales microbe to form a second mixture and incubating the second mixture at less than 28° C., wherein the donor microbe contains a nucleic acid fragment and the recipient microbe does not contain the nucleic acid fragment;
    detecting a recipient microbe containing the nucleic acid fragment, wherein the frequency of transduction is at least $10^{-5}$-', wherein the detection of the recipient microbe indicates the phage is a transducing phage; and
    isolating the transducing phage.
12. The transducing phage of claim 11 wherein the at least one nucleic acid fragment comprises a nucleic acid fragment selected from the group consisting of at least one non-coding region and at least one coding region or a portion thereof.
13. The transducing phage of claim 11 wherein the donor Actinomycetales or the recipient Actinomycetales is a Streptomycetaceae.
14. The transducing phage of claim 13 wherein the Streptomycetaceae is a a Streptomyces.
15. The transducing phage of claim 11 wherein the donor Actinomycetales and the recipient Actinomycetales is selected from the group consisting of spores, mycelial fragments, germlings, protoplasts, and mixtures thereof.
16. The transducing phage of claim 11 further comprising reducing superinfection of the recipient microbe containing the nucleic acid fragment.
17. The transducing phage of claim 16 wherein reducing superinfection comprises reducing superinfection killing of the recipient microbe containing the nucleic acid fragment.
18. The transducing phage of claim 17 wherein reducing superinfection killing of the recipient microbe containing the nucleic acid fragment comprises treating the lysate prior to combining it with the recipient microbe.
19. The transducing phage of claim 18 wherein treating the lysate comprises exposing it to ultraviolet radiation.
20. The transducing phage of claim 17 wherein reducing superinfection killing of the recipient microbe containing the nucleic acid fragment comprises treating the recipient microbe containing the nucleic acid fragment with a chelator.
21. The transducing phage of claim 20 wherein the chelator comprises citrate.
22. The transducing phage of claim 11 wherein the phage is a generalized transducing phage.
23. The transducing phage of claim 11 wherein the phage is a specialized transducing phage.
24. The transducing phage of claim 11 wherein the phage is obtained from the group consisting of soil, water, organic material, decomposing organic material, and volcanic ash.
25. The transducing phage of claim 24 wherein the phage is plaque purified prior to forming the first mixture.
26. A transducing particle isolated by a method comprising:
    combining a phage with a donor Actinomycetales microbe to form a first mixture and incubating the first mixture under conditions such that a lysate is produced;
    combining the lysate with a recipient Actinomycetales microbe to form a second mixture and incubating the second mixture at less than 28° C., wherein the donor microbe contains a nucleic acid fragment and the recipient microbe does not contain the nucleic acid fragment;

detecting a recipient microbe containing the nucleic acid fragment, wherein the frequency of transduction is at least $10^{-5}$, wherein the detection of the recipient microbe indicates the lysate contains a transducing particle; and isolating the transducing particle.

27. The transducing particle of claim 26 wherein the at least one nucleic acid fragment comprises a nucleic acid fragment selected from the group consisting of at least one non-coding region and at least one coding region or a portion thereof.

28. The transducing particle of claim 26 wherein the donor Actinomycetales or the recipient Actinomycetales is a Streptomycetaceae.

29. The transducing particle of claim 28 wherein the Streptomycetaceae is a Streptomyces.

30. The transducing particle of claim 26 wherein the donor Actinomycetales and the recipient Actinomycetales is selected from the group consisting of spores, mycelial fragments, germlings, protoplasts, and mixtures thereof.

31. The transducing particle of claim 26 further comprising reducing superinfection of the recipient microbe containing the nucleic acid fragment.

32. The transducing particle of claim 31 wherein reducing superinfection comprises reducing superinfection killing of the recipient microbe containing the nucleic acid fragment.

33. The transducing particle of claim 32 wherein reducing superinfection killing of the recipient microbe containing the nucleic acid fragment comprises treating the lysate prior to combining it with the recipient microbe.

34. The transducing particle of claim 33 wherein treating the lysate comprises exposing it to ultraviolet radiation.

35. The transducing particle of claim 32 wherein reducing superinfection killing of the recipient microbe containing the nucleic acid fragment comprises treating the recipient microbe containing the nucleic acid fragment with a chelator.

36. The transducing particle of claim 35 wherein the chelator comprises citrate.

37. The transducing particle of claim 26 wherein the phage is a generalized transducing phage.

38. The transducing particle of claim 26 wherein the phage is a specialized transducing phage.

39. The transducing particle of claim 26 wherein the phage is obtained from the group consisting of soil, water, organic material, decomposing organic material, and volcanic ash.

40. The transducing particle of claim 39 wherein the phage is plaque purified prior to forming the first mixture.

41. A method of producing a phage lysate, the method comprising:

combining an isolated transducing phage with a donor Actinomycetales microbe to form a phage-donor microbe mixture, wherein the isolated transducing phage can transfer at least one nucleic acid fragment from a donor Actinomycetales microbe to a recipient Actinomycetales microbe at a temperature of less than 28° C., wherein the frequency of transduction is at least $10^{-5}$, and incubating the phage-donor microbe mixture to produce a phage lysate comprising a transducing phage.

42. A phage lysate comprising a transducing phage, wherein the transducing phage can transfer at least one nucleic acid fragment from a donor Actinomycetales microbe to a recipient Actinomycetales microbe at a temperature of less than 28° C., wherein the frequency of transduction is at least $10^{-5}$.

* * * * *

UNITED STATES PATENT AND TRADEMARK OFFICE
CERTIFICATE OF CORRECTION

PATENT NO. : 6,589,732 B2
DATED : July 8, 2003
INVENTOR(S) : Westpheling et al.

It is certified that error appears in the above-identified patent and that said Letters Patent is hereby corrected as shown below:

Column 1,
Line 12, delete "1021RR093161" and insert -- MCB-9722960 --

Column 22,
Line 17, delete "$10^{-5}$-'" and insert -- $10^{-5}$ --

Signed and Sealed this

Fourth Day of May, 2004

JON W. DUDAS
*Acting Director of the United States Patent and Trademark Office*